(12) United States Patent
Kaiser et al.

(10) Patent No.: US 7,542,955 B2
(45) Date of Patent: Jun. 2, 2009

(54) EXERCISE TEST INTERPRETATION

(75) Inventors: Willi Kaiser, Emmendingen (DE); Martin Findeis, Freiburg (DE); Brian J. Young, Germantown, WI (US)

(73) Assignee: The General Electric Company, Schenectady, NY (US)

( * ) Notice: Subject to any disclaimer, the term of this patent is extended or adjusted under 35 U.S.C. 154(b) by 267 days.

(21) Appl. No.: 11/372,852

(22) Filed: Mar. 10, 2006

(65) Prior Publication Data
US 2007/0239647 A1 Oct. 11, 2007

(51) Int. Cl.
*G06N 5/02* (2006.01)

(52) U.S. Cl. .............................. 706/46; 706/50; 706/47; 600/301; 600/374; 600/382; 600/520

(58) Field of Classification Search ............. 706/45–47, 706/50, 60–61; 600/301, 372–374, 382, 600/454, 467, 475, 479, 481, 486, 508–509, 600/520, 533, 534
See application file for complete search history.

(56) References Cited

U.S. PATENT DOCUMENTS

| | | | | |
|---|---|---|---|---|
| 5,788,640 A * | 8/1998 | Peters | ........................ | 600/483 |
| 5,850,221 A * | 12/1998 | Macrae et al. | .............. | 715/853 |
| 6,004,276 A | 12/1999 | Wright et al. | | |
| 6,210,301 B1 * | 4/2001 | Abraham-Fuchs et al. | ..... | 482/8 |
| 6,387,053 B1 * | 5/2002 | Pessenhofer | ................ | 600/531 |
| 6,656,125 B2 * | 12/2003 | Misczynski et al. | ......... | 600/508 |
| 6,863,656 B2 * | 3/2005 | Lurie | .......................... | 600/481 |
| 6,993,377 B2 * | 1/2006 | Flick et al. | .................. | 600/509 |
| 7,107,095 B2 * | 9/2006 | Manolas | ..................... | 600/513 |
| 7,218,968 B2 * | 5/2007 | Condie et al. | ................. | 607/59 |
| 2003/0163355 A1 * | 8/2003 | Kaiser et al. | .................... | 705/3 |
| 2004/0059205 A1 * | 3/2004 | Carlson et al. | .............. | 600/310 |
| 2004/0249299 A1 * | 12/2004 | Cobb | ......................... | 600/529 |
| 2005/0126567 A1 * | 6/2005 | Lurie | .................... | 128/203.11 |
| 2005/0171443 A1 * | 8/2005 | Gorenberg et al. | .......... | 600/490 |
| 2007/0060803 A1 * | 3/2007 | Liljeryd et al. | .............. | 600/301 |

FOREIGN PATENT DOCUMENTS

| | | |
|---|---|---|
| EP | 1 378 853 A1 | 1/2004 |
| WO | WO 01/28416 A1 | 4/2001 |
| WO | WO 03/020128 A2 * | 3/2003 |

OTHER PUBLICATIONS

"Automatic Learning of Rules", Journal of Electrocardiology vol. 29 Supplement, Kaiser et al., pp. 17-20.
Search Report dated Jun. 25, 2007.
"Automatic Learning of Rules", Journal of Electrocardiology vol. 29 Supplement, Kaiser et al., pp. 17-20, 1996.

* cited by examiner

*Primary Examiner*—David R Vincent
*Assistant Examiner*—Omar F Fernandez Rivas
(74) *Attorney, Agent, or Firm*—Andrus, Sceales, Starke & Sawall, LLP

(57) ABSTRACT

A system and method for the efficient implementation of a complex exercise test is disclosed. A rule interpreter synthesizes interpretation statements based upon the processing of collected physiological data and user entered data with a series of exercise test interpretation rules. These statements aid a clinician in interpreting exercise test results by identifying detected abnormal or borderline conditions.

16 Claims, 3 Drawing Sheets

TEST SUMMARY

PATIENT INFO — 18

- 62 years Caucasian Female — 40
- 164 cm 72.0 kg — 46 — 42
- Beta Blocker? (Yes) — 48
- Angina? (No) — 50
- Test Type: Stress Test — 52
- Test Equip: Treadmill — 54

MEASUREMENT RESULTS — 16

- 20W/min  Total Exercise Time 06:04 — 56
- HR (Baseline, Max.): 87, 131 bpm — 58 — 60
- BP (Baseline, Max.):-/-,-1/-1 mmHg  Max. Load: 140 Watt
- Arrhythmia:  A: 4, VBIG: 4, PVC: 31, PSVC: 3, CPLT: 1 — 62
- ST/HR Slope: 10.59 μV/bpm (V3) — 64
- ST/HR Index: 7.15 μV/bpm (V3) — 66
- ST/HR Hysteresis: 0.21 mV (V3) — 68
- HR-Recovery: 38 bpm — 70
- ST (Baseline, Max.): 0.07, -0.32 mV (V3)
- Max. ST in peak exercise: -0.31 mV (V3)
- Max. ST in recovery: -0.32 mV (V3)
- Max. TWA: 12 μV (V3) — 72

TEST INTERPRETATION — 20

- increased risk of morbidity / mortality — 24
  - because Duke Treadmill Score (DTS) <=-10 — 27
- chronotropic incompetence — 25
  - because (HRpeak-HRrest)/(220-age-HRrest) <=0.8 — 28
  - Possible casue: medication beta-blockers — 26
- ischemia, probably caused by coronary artery disease   (lateral, anterior) — 34
  - because ST/HR hystersis >=0.01 mV in [V3 V4 V5] and — 29
  - ST/HR slope >=2.4  V/bpm in [V3 V4] — 30
- abnormal exercise test response — 32

36

PRINT

LOCAL DB

HOME

EXERCISE TEST INTERPRETATION

BACKGROUND OF THE INVENTION

Computerized electrocardiographic (ECG) interpretation has become widely accepted in the medical field. Physicians frequently utilize this technique as a back-up to their own interpretation of ECG results, or as a check to ensure that abnormal ECG waveform morphologies have not been overlooked. The interpretation of ECG waveforms is difficult and even physicians may be misled due to the complexity of the analysis that must be performed. In many instances, multiple tests or algorithms must be utilized to obtain a conclusive result as the result of a single test may fail to distinguish correctly between healthy and pathological ECGs or between different ECG pathologies.

Exercise tests utilizing a treadmill or a stationary bicycle have increased in popularity as a useful diagnostic tool of cardiac health. One advantage of exercise tests over resting ECG tests is the increased number of physiological measurement values that may be obtained as the body is put under a stress and then recovers from that stress. These physiological measurement values have the power to predict morbidity/mortality rates, coronary artery disease, and also can describe the functional exercise response of a patient. An ideal physician would take all of these physiological measurements from the exercise stress test and compare the measurements to the known limits for each of these values as determined by scientific experiments to come to a complete assessment of the patient's health as determined by the exercise test.

Due to recent increases in the number of useful physiological measurement values and applicable analysis algorithms and limits, it has become very difficult for a physician to know and apply everything that is needed for a complete assessment of the exercise test. Additionally, it is increasingly difficult for the physician to understand the meaning of an algorithm result and to identify pathologies that are identified with combinational algorithms that compare limits of multiple measurement values. Therefore, it is desirable in the field of ECG analysis for a system that provides a complete assessment of an exercise test to help a physician manage the high number of physiological measurement values with increasingly complex diagnostic algorithms.

SUMMARY OF THE INVENTION

Due to the increasing numbers of exercise test analysis options and the complexity of these diagnostic algorithms, it is therefore advantageous to develop a computerized exercise test interpretation system as in the present invention. A database of exercise test interpretation rules is created whereby a rule interpreter may take the physiological measurement values recorded from an exercise test combined with additional clinician-entered data and process this information with the desired exercise test interpretation rules to produce an exercise test interpretation. This interpretation may comprise interpretation statements along with additional reasoning texts that particularize and point out the specific exercise test interpretation rules that were the cause for the resultant interpretation.

The present invention facilitates the implementation of an exercise stress test by allowing the rule interpreter to guide the interpreting physician with the exercise test measurements by pointing out patient conditions that the physician should further investigate, providing support to physician interpretations of exercise measurement values, and ensuring that abnormal exercise measurement values are not overlooked by the physician. In an embodiment of the present invention, the interpretation statements also include physiological location information to supplement the interpretation statements regarding cardiac fitness. In a still further embodiment of the present invention, an exercise test interpretation may comprise either the interpretation statements or the reasoning texts as selected by the physician.

Various other features, objects and advantages of the invention will be made apparent from the following description taken together with the drawings.

BRIEF DESCRIPTION OF THE DRAWINGS

The drawings illustrate the best mode presently contemplated of carrying out the invention. In the drawings:

FIG. 3 depicts a graphical display of an embodiment of the exercise test interpretation of the present invention.

DETAILED DESCRIPTION OF THE INVENTION

Figure 1:
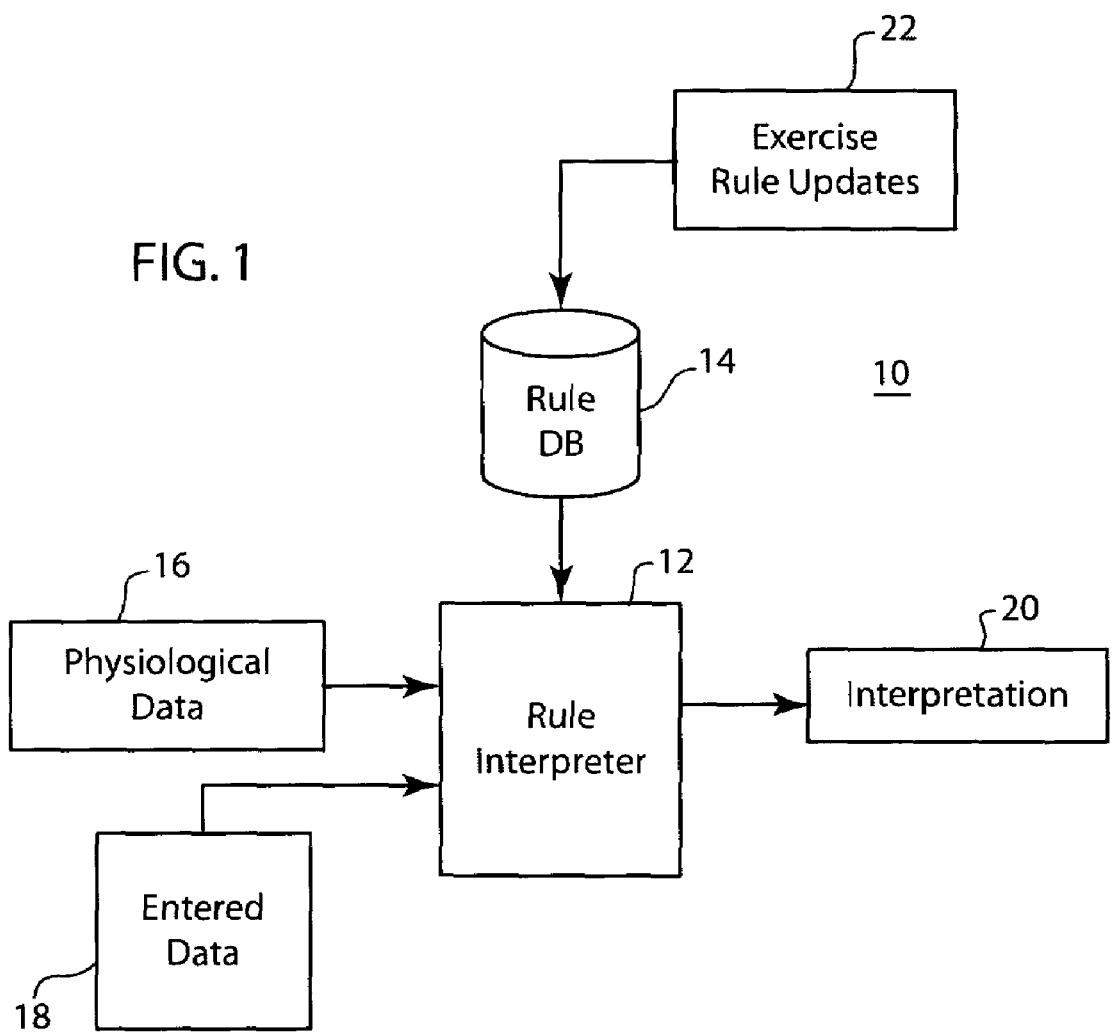
FIG. 1 is a schematic diagram of the operation of the exercise test interpretation of the present invention.

FIG. 1 depicts a flowchart of the operation of the present invention. A clinician's analysis of the results recorded from a patient's exercise stress test is facilitated by the exercise test interpretation system of the present invention 10. This analysis is provided through the use of a rule interpreter 12. The rule interpreter 12 uses exercise test interpretation rules stored in a rule database 14 to interpret the results of an exercise stress test based upon both the measured physiological data 16 recorded from the patient during the exercise test as well as additional patient information 18 that is added by the clinician. The rule interpreter 12 applies the selected rules from the rule database 14 to the physiological data 16 and the clinician-entered data 18 to create an interpretation 20 of the results of the exercise test.

Figure 2:
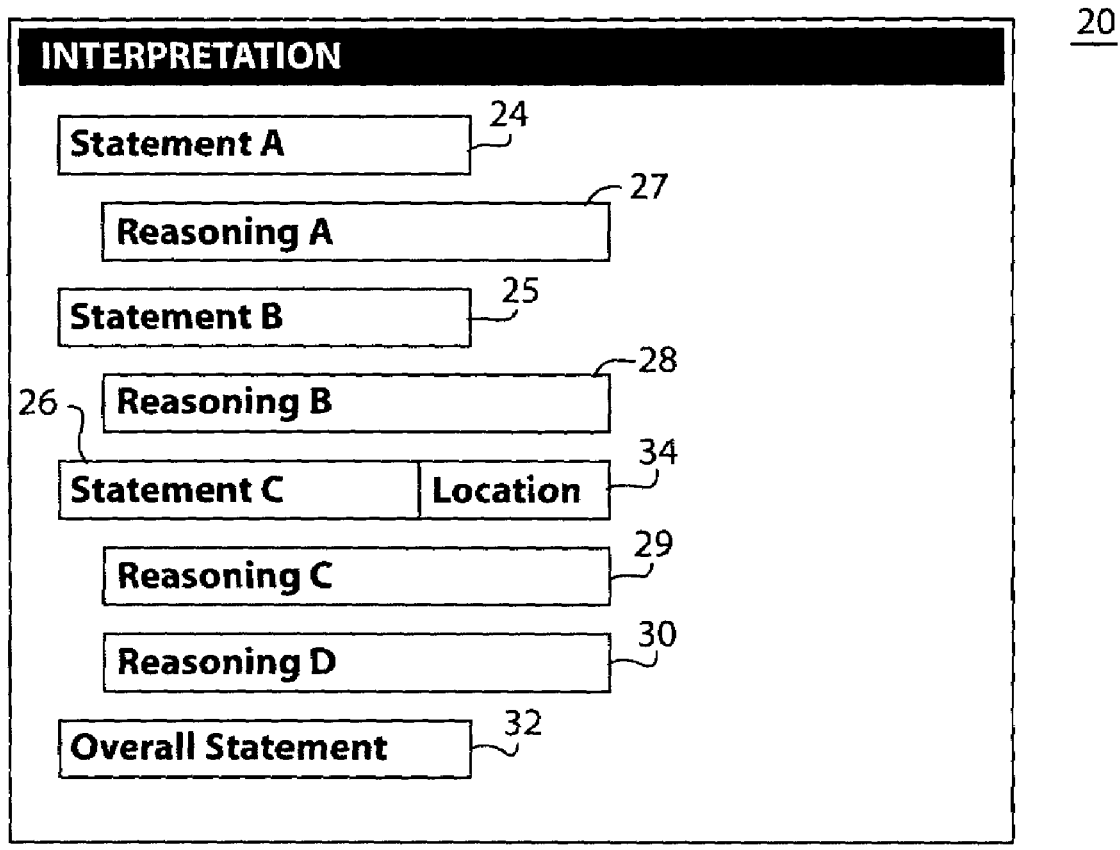
FIG. 2 depicts a generalized depiction of an embodiment of the exercise test interpretation display.

FIG. 2 depicts an interpretation 20 of an embodiment of the present invention. The interpretation 20 comprises a plurality of interpretation statements depicted here as statements A-C, 24-26 respectively, and a plurality of associated reasoning texts 27-30, respectively. In an embodiment of the present invention, the interpretation statements 24-26 are divided into three statement groups for analysis. These statement groups may comprise, but are not limited to, risk prediction statements, cardiac functional response statements, and coronary artery disease statements. Additionally, an overall summary statement 32 may be included in the interpretation 20.

An exercise test interpretation 20 may comprise any number of interpretation statements 24-26 from any statement grouping as is identified by the rule interpreter 12 in analyzing the physiological and entered data 16, 18. Each rule that is stored in the rule database 14 represents a pathological condition resulting in an abnormal or borderline exercise test. This rule may comprise value limits and/or ranges for physiological data values or may comprise a Boolean statement combining one or more values and/or value ranges or limits.

The fulfillment of a rule results in the textual display of an interpretation statement 24-26. The rule that was fulfilled to trigger the display of the statement 24-26 is displayed as the associated reasoning text 27-30. Often, as with statement A, each statement has one reasoning text, Reasoning A 27. However, for example, statement C 26 is supported by two reasoning texts, Reasoning C 29 and Reasoning D 30. This depicts a situation in which two rules were fulfilled that resulted in the same diagnostic statement. Additionally, in an embodiment of the invention, in cases of the detection of coronary artery disease, where it is possible to determine the location of the detected abnormality, in an embodiment of the present invention this location is also displayed as a location statement 34 in the interpretation statement 24. If, for example, the exercise test was performed with a traditional 12-lead ECG, then the affected areas of the heart may be determined by comparing the signals of the precordial electrodes. In an embodiment of the present invention, the overall statement 32 indicates if any abnormal or borderline condition has been detected by the exercise test, or if the physiological data appears to be normal.

Referring back to FIG. 1, the clinician enters information about the patient and the exercise test to the rule interpreter for use in analyzing the exercise test. This clinician-entered data 18 may comprise standard physiological data such as age, gender, race, height, and weight but may also include, in an embodiment of the invention, patient information such as whether the patient is currently using a beta blocker or if the patient is or has experienced angina. In an embodiment of the invention, additional information may be included such as the type of the test being performed as well as the test equipment and the test duration. These additional test information values provide information for the selection of the proper exercise test rules from rule database 14 to apply in the current test. This may be important as some exercise test algorithms such as the Duke Treadmill Score (DTS) or the Metabolic Equivalent (MET) require this additional test information, to compute the values associated with these tests.

As the patient undergoes the exercise test, physiological measurements 16 are recorded and then reported to the rule interpreter 12. The physiological measurements 16 may include recorded data such as the detected raw 5-lead or 12-lead ECG measurements but may also include a variety of calculated values representing additional physiological measurements. These calculated values may also include information processed from the recorded ECG waveforms. This processed information may include ST depression, detection of arrhythmia, or the direction of the ST/HR loop, but many other processed values are envisioned as being within the present invention. It is understood that the necessary physiological measurements 16 that are recorded and sent to rule interpreter 12 is dependent upon the requirements of the rules in the exercise test rule database 14.

As stated above, the exercise test rules in rule database 14 are comprised of physiological measurement limits or ranges that signify a particular pathology. These rules may also comprise Boolean statements comprising one or more physiological measurement limit statements or user entered data values. In an embodiment of the present invention, the rules are divided into groups based upon the types of pathology to which they are directed. In the risk prediction group, rules such as a DTS of less than −10 or heart rate recovery of less than 12 bpm, indicate a risk of morbidity or mortality. On the other hand, if T-wave alternans are greater than or equal to 30 $\mu V$, then there exists an increased risk of malignant arrhythmias. In the group of rules for determining cardiac functional response, an embodiment of the present invention may use a rule such as if MET's are $\leq$ to 5, then the patient has an insufficient exercise capacity. Alternatively, if the heart rate used is less $\leq 0.8$, then the patient is experiencing chronotropic incompetence. Finally, rules that address the likelihood of coronary artery disease may include an ST depression of $\geq 1$ millimeter, an ST/HR slope of $\geq 2.4$ microvolts per BPM, or an ST/HR loop that is counterclockwise, or ST/HR hysteresis that is $\geq 0.25$ millimeters. The rules for likelihood of coronary artery disease also include specific location indicators based upon the ECG leads in which the rules are fulfilled to also indicate the relative location of the CAD. It is understood that these values and descriptions are not intended to be limiting on the scope of he present invention, but rather are exemplary of the rules that may be used with the present invention.

FIG. 3 is an exemplary depiction of a graphical user interface (GUI) 36 of an embodiment of the present invention. The GUI 36 comprises sections for clinician-entered data 18, physiological measurement data 16, and the resulting exercise test interpretation 20. The clinician-entered data 18 includes information regarding the patient's age 38, gender 40, race 42, height 44, and weight 46. Clinician-entered data 18 includes additional information, such as use of a beta blocker 48 and angina experience 50, as well as exercise test information, such as test type 52 and test equipment 54. Physiological measurement data 16 may include total exercise time 56, as well as data such as heart rate 58, blood pressure 60, arrhythmia detection 62, ST/HR hysteresis 68, HR recovery 70, and Maximum TWA 72.

The exercise test interpretation section 20 depicts in exemplary detail the diagram depicted in FIG. 2. In reading the interpretation 20, statement 24 indicates that the patient has an increased risk of morbidity/mortality. The associated reasoning 27 states that this conclusion is based upon a DTS of $\leq -10$, which was previously stated as a potential exercise test interpretation rule. In the statement concerning CAD risk 26, there are multiple reasoning statements 29, 30 that indicate that multiple CAD detection rules were fulfilled. Additionally, location indication 34 identifies the areas of the heart affected by CAD. Finally, the overall statement 32 identifies that this patient has had an abnormal exercise test response.

Referring back to FIG. 1, in an embodiment of the present invention, a clinician and/or hospital administrator may include exercise rule updates 22 to the exercise test rule database 14. These exercise rule updates would allow the rule database to improve along with the science in this field. It would also allow for an institution to determine desirable standardized tests to be performed in similar situations as well as allow a clinician the freedom and/or flexibility to include his own additional rules.

In a still further embodiment of the present invention, the clinician is allowed to select the desired rules from the exercise test rule database 14 to be used in the rule interpreter 12 for each exercise test there is performed. This allows for the clinician to create a more individually tailored test for each patient based upon the condition of the patient and/or the medical concern surrounding that patient.

In a further embodiment of the present invention, the exercise test interpretation may include only the interpretation statements 24 or only the reasoning statements 26. This option allows the clinician to tailor the results of the exercise test interpretation to be presented in a way that is most desirable for his overall diagnosis of the patient's condition.

This written description uses examples to disclose the invention, including the best mode and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements of insubstantial differences from the literal language of the claims.

Various alternative and embodiments are contemplated as being within the scope of the following claims, particularly pointing out and distinctly claiming the subject matter regarded as the invention.

We claim:

1. An integrated system for interpreting the results of an exercise test being performed on a patient by a clinician, said system comprising:
   a patient monitor that receives a plurality of physiological parameter data from the patient during the exercise test;
   a rule database comprising a plurality of exercise test interpretation rules with physiological parameter data value criteria, wherein a plurality of combinations of one or more of the exercise test interpretation rules define a pathological condition;
   a rule interpreter that receives the plurality of exercise test interpretation rules from the rule database and the plurality of physiological parameter data from the patient, wherein the rule interpreter evaluates the plurality of exercise test interpretation rules with the plurality of physiological parameter data from the patient and produces an interpretation statement and a reasoning text for each exercise test interpretation rule for which the physiological parameter data value criteria is fulfilled; and
   an exercise test interpretation display that receives the interpretation statement and the reasoning text from the rule interpreter and presents the interpretation statement and the reasoning text associated with the interpretation statement, wherein the interpretation statement is a textual description of a pathological condition afflicting the patient as identified by the fulfillment of one or more physiological parameter data value criteria, and the reasoning text is a textual description of the combination of one or more exercise test interpretation rules for which the physiological parameter data value criteria was fulfilled to result in the received interpretation statement.

2. The integrated system of claim 1 wherein the physiological parameter data value criteria comprise value limits.

3. The integrated system of claim 2 wherein the physiological parameter data value criteria further comprise Boolean statements.

4. The integrated system of claim 1 wherein the interpretation statement further comprises a location statement that identifies an anatomical location within the patient that is afflicted by the pathological condition identified by the interpretation statement.

5. The integrated system of claim 4 wherein the exercise test interpretation display further presents a summary statement that is a textual description of the normality of the pathological condition identified in the interpretation statement.

6. The integrated system of claim 1, further comprising a plurality of interpretation statements, the plurality of interpretation statements including:
   a risk prediction statement that is a textual description of a physiological risk afflicting the patient;
   a cardiac functional response statement that is a textual description of a functional evaluation of the patient's cardiac system; and
   a coronary artery disease statement that is a textual description of the patient's indicated coronary artery disease.

7. The integrated system of claim 6, wherein the coronary artery disease statement further comprises a location statement that identifies an anatomical location within the patient that is afflicted by the identified coronary artery disease.

8. The integrated system of claim 6, wherein each of the risk prediction statement, the cardiac functional response statement, and the coronary artery disease statement describe pathological conditions defined by a plurality of combinations of one or more of the exercise test interpretation rules.

9. A computer implemented method of interpreting physiological data collected from a patient undergoing an exercise test, the method comprising the steps of:
   collecting the physiological data from the patient;
   a rule interpreter of a computer retrieving a plurality of exercise test interpretation rules from a database, each of the exercise test interpretation rules defining a pathological condition with a plurality of combinations of one or more physiological data value criteria;
   the rule interpreter evaluating the plurality of exercise test interpretation rules with the collected physiological data from the patient;
   upon the fulfillment of the physiological data value criteria of the exercise test interpretation rule by the collected physiological data, the rule interpreter generating an exercise test interpretation statement and a reasoning text; and,
   presenting the exercise test interpretation statement and the reasoning text, associated with the exercise interpretation statement, on a graphical display;
   wherein the exercise test interpretation statement is a textual description of the pathological condition afflicting the patient as identified by the fulfillment of a combination of one or more of the physiological data value criteria and the reasoning text is a textual description of the combination of one or more of the physiological data value criteria that were fulfilled to result in the presented exercise text interpretation statement.

10. The computer implemented method of exercise test interpretation of claim 9 further comprising the steps of:
    the rule interpreter receiving patient data and exercise test data;
    combining the patient data and exercise test data with the physiological data; and
    evaluating the plurality of exercise test interpretation rules with the patient data and exercise test data;
    wherein the plurality of exercise test interpretation rules require patient data and exercise data in the physiological data value criteria.

11. The computer implemented method of claim 9 further comprising the step of presenting a summary statement on the graphical display, the summary statement indicative of the abnormality of the exercise test.

12. The computer implemented method of claim 11 further comprising: presenting a location statement on the graphical display in visual association with the exercise test interpretation statement, wherein the location statement is a textual statement of an anatomical location within the patient that is afflicted by the pathological condition identified by the interpretation statement.

13. The computer implemented method of claim 9, wherein the exercise text interpretation statement is selected from a list comprising: a risk prediction statement that is a textual description of a physiological risk afflicting the patient, a cardiac functional response statement that is a textual description of an evaluation of a patient's cardiac function; and a coronary artery disease statement that is a textual description of the patient's indicated coronary artery disease.

14. The computer implemented method of claim 13, further comprising presenting a plurality of exercise test interpretation statements, wherein the plurality of exercise test interpretation statements includes a risk prediction statement, a cardiac function response statement, and a coronary artery disease statement.

15. The computer implemented method of claim 14, wherein the coronary artery disease statement further comprises a location statement that textually identifies an anatomical location within the patient that is afflicted by the identified coronary artery disease.

16. The computer implemented method of claim 14 wherein each of the risk prediction statement, cardiac functional response statement, and coronary artery disease statement describe pathological conditions defined by a plurality of combinations of one or more of the exercise test interpretation rules.

* * * * *